(12) United States Patent
Booher et al.

(10) Patent No.: US 8,637,271 B2
(45) Date of Patent: Jan. 28, 2014

(54) POLYMERIC INDICATORS FOR DETECTING THE PRESENCE OF METABOLIC BYPRODUCTS FROM MICROORGANISMS

(75) Inventors: Jon Booher, Advance, NC (US); Joel R. Gorski, Perrysburg, OH (US)

(73) Assignee: Indicator Systems International, Inc., Newport Beach, CA (US)

( * ) Notice: Subject to any disclaimer, the term of this patent is extended or adjusted under 35 U.S.C. 154(b) by 576 days.

(21) Appl. No.: 12/741,268

(22) PCT Filed: Nov. 5, 2008

(86) PCT No.: PCT/US2008/082498
§ 371 (c)(1),
(2), (4) Date: Oct. 29, 2010

(87) PCT Pub. No.: WO2009/061831
PCT Pub. Date: May 14, 2009

(65) Prior Publication Data
US 2011/0042344 A1     Feb. 24, 2011

Related U.S. Application Data

(60) Provisional application No. 60/986,444, filed on Nov. 8, 2007.

(51) Int. Cl.
*B29D 22/00*     (2006.01)
*C12Q 1/04*     (2006.01)

(52) U.S. Cl.
USPC .......................................... 435/34; 428/36.6

(58) Field of Classification Search
USPC ....................................................... 428/36.6
See application file for complete search history.

(56) References Cited

U.S. PATENT DOCUMENTS

| | | |
|---|---|---|
| 3,899,295 A | 8/1975 | Halpern |
| 3,946,611 A | 3/1976 | Larsson |
| 4,094,642 A | 6/1978 | Sumimoto et al. |
| 4,197,947 A | 4/1980 | Zaidi |
| 4,205,043 A | 5/1980 | Esch et al. |
| 4,222,745 A | 9/1980 | Cloyd |
| 4,269,804 A | 5/1981 | Kring |
| 4,271,121 A | 6/1981 | Diller et al. |
| 4,285,697 A | 8/1981 | Neary |
| 4,328,181 A | 5/1982 | Anders et al. |
| 4,746,616 A | 5/1988 | Honigs et al. |
| 4,987,849 A | 1/1991 | Sherman |
| 5,053,339 A | 10/1991 | Patel |
| 5,096,813 A | 3/1992 | Krumhar et al. |
| 5,128,106 A | 7/1992 | Buschmann et al. |
| 5,215,956 A | 6/1993 | Kawashima |
| 5,228,573 A | 7/1993 | Pavelle et al. |
| 5,407,829 A | 4/1995 | Wolfbeis et al. |
| 5,437,622 A | 8/1995 | Carion |
| 5,498,528 A | 3/1996 | King |
| 5,629,360 A | 5/1997 | Askari et al. |
| 5,753,285 A | 5/1998 | Horan |
| 5,916,585 A | 6/1999 | Cook |
| 5,922,281 A | 7/1999 | Elgas et al. |
| 6,149,952 A | 11/2000 | Horan |
| 6,391,626 B1 | 5/2002 | Adams et al. |
| 6,495,368 B1 | 12/2002 | Wallach |
| 6,562,297 B1 | 5/2003 | Bonstein et al. |
| 6,589,761 B1 | 7/2003 | Freadman et al. |
| 6,924,147 B2 | 8/2005 | Kelly et al. |
| 7,014,816 B2 | 3/2006 | Miller et al. |
| 7,183,455 B2 | 2/2007 | Utsugi |
| 7,749,531 B2 | 7/2010 | Booher |
| 2003/0060479 A1 | 3/2003 | Brown et al. |
| 2003/0064422 A1 | 4/2003 | McDevitt et al. |
| 2003/0199783 A1 | 10/2003 | Bloom et al. |
| 2003/0203011 A1 | 10/2003 | Abuelyaman et al. |
| 2004/0044299 A1 | 3/2004 | Utsugi |
| 2004/0115319 A1 | 6/2004 | Morris et al. |
| 2007/0276207 A1 | 11/2007 | Eagland et al. |

OTHER PUBLICATIONS

Luo F., Liu Z.-H., Chen T.-L., and Gong B.-L. "Cross-linked Polyvinyl Alcohol pH Sensitive Membrane Immobilized with Phenol Red for Optical pH Sensors". Chinese Journal of Chemistry 2006, vol. 24, 341-344.*

Lambert et al., "Improved Synthesis of Polymethoxytriphenylmethanols for use as One-colour PH Indicators." Analyst. 1981, 106:1013-1016.

Liu et al., "Facile Synthesis, Characterization, and Potential Applications of Two Kinds of Polymeric pH Indicators: Phenolphthalein Formaldehyde and o-Cresolphthalein Formaldehyde." Published online in Wiley InterScience (www.inerscience.wiley.com), (2004) :1019-1027.

Rubin et al., "The Economic Impact of *Staphylococcus aureus* Infection in New York City Hospitals: Emerging Infectious Diseases." Emerging Infectious Diseases, (1999) 5(1):9-17.

* cited by examiner

*Primary Examiner* — Allison Ford
*Assistant Examiner* — Michelle F Paguio Frising
(74) *Attorney, Agent, or Firm* — Foley & Lardner LLP

(57) ABSTRACT

Polymeric indicators are provided for visually monitoring, detecting, and/or determining the presence of metabolic byproducts from harmful or potentially harmful microorganisms.

2 Claims, No Drawings

POLYMERIC INDICATORS FOR DETECTING THE PRESENCE OF METABOLIC BYPRODUCTS FROM MICROORGANISMS

This application is a U.S. national stage of international application PCT PCT/US08/82498 filed Nov. 5, 2008; which claims priority to and the benefit of U.S. Provisional Application Ser. No. 60/986,444, filed Nov. 8, 2007.

TECHNICAL FIELD

This invention relates generally to polymeric indicators, their preparation, and their uses for detecting the presence of metabolic byproducts from microorganisms. Such polymeric indicators have covalently bound thereto hydroxy phenyl pH indicators.

BACKGROUND

The presence of undesirable microbial contamination in food products intended for consumption is of significant concern to manufacturers, farmers, packagers, food distributors, wholesalers, retailers, consumers, and to worldwide public health. A particularly worrisome concern is bacterial contamination in packages containing food products for human consumption. The United States boasts of the safest food in the world; however, each year one in four citizens suffers from a food borne illness and some 5,000 die from something they have eaten. According to the Center for Disease Control and Prevention, each year in the United States, 76 million people contract some kind of food borne illness, 325,000 are hospitalized and 5,000 fatalities occur due to microbial contamination of consumed food. In Third World countries it has been estimated that bacterial contaminated food and water kills over two million children each year. Despite those numbers, most food borne infections are undiagnosed and unreported.

Packaging of perishable and edible food products that may be susceptible to bacterial contamination has concentrated primarily on the prevention of bacterial growth of these products as opposed to the detection of bacterial growth in these products. Hence, there is a need for an improved method for making packaging material for determining the presence or absence of contaminating microorganisms in a package.

When the packaging/wrapping element has been used for detection of microbial growth in the food stuff, such elements typically had a pH indicator entrapped in the polymer composition. See, e.g., U.S. Pat. Nos. 5,753,285 and 6,495,368 which disclose dispersion of the indicator into the polymer blend for use in food wraps. The pH indicator is sensitive to byproducts produced by microbial growth on/in the food stuff and a change in color of the indicator is taken as a measure of the extent of microbial growth. Nevertheless, such packaging elements are susceptible to leaching of the pH indicator into the food thereby contaminating the food and as such are not favored.

The use of pH indicators covalently bound to a polymeric matrix has been disclosed by, for example, Adams, et al., U.S. Pat. No. 6,391,626 wherein a functional group of the pH indicator is directly bound to a functional group of the polymeric matrix. Specifically disclosed is the covalent bonding of [2-(2,4-dinitrophenylazo)-6-(N-methyl-N-(2-hydroxysulfonyl-oxy-ethylsulfonyl)amido]-1-naphthol-3-sulfonic acid (DNSA) to polyvinyl alcohol (PVOH). It would appear that one possible covalent bond formed would be a sulfonoxy bond between the hydroxyl group of the PVOH and the sulfonic acid of DNSA.

Such direct binding of the pH indicator is limited by several factors including the presence of a suitable functionality on the pH indicator that can bind to the polymeric matrix without loss of its pH indicating properties; the stability of the resulting bond during storage and under aqueous acidic or basic conditions, and the level of indicator bound to the polymer. In the last case, Adams reports that the 500 mg of indicator is bound to 100 g of polymer (a 200:1 ratio of polymer to indicator). Further, it is recognized in the art that the use of common ester or acidamide covalent bonds between the pH indicator and the polymeric resin is less than ideal as these bonds are not stable in either acidic or alkaline environments.

Covalent binding of pH indicators through a linker group has been disclosed by Liu, et al., Journal of Polymer Science Vol. 43 1019-1027 (2006) pp. 1019-1027 and Sensors and Actuators B 107 (2005) pp. 311-315. These references disclose the formation of intermediates formed by reacting phenolphthalein, o-cresolphthalein, and phenol red with formaldehyde. These intermediates in turn are reacted with PVOH in the presence of DMSO at 100° C. to provide a defined covalent linkage. However, these references do not disclose the use of such covalently bound pH indicators for use in food storage and detection of microbial growth. In point of fact, the use of DMSO as a solvent during bonding of the indicator to the PVOH through the linker is counter-intuitive to use of the resulting polymeric film to wrap food stuffs as DMSO is known to impart a bitter taste (Merck Index, 12$^{th}$ Ed. P. 3309 (1996)). Accordingly, any residual DMSO in the product could contaminate the food rendering it non-sellable.

SUMMARY OF THE INVENTION

The present invention provides polymeric compositions comprising polyvinyl alcohol PVOH and a plurality of hydroxy phenyl pH indicator moieties stably attached thereto through a covalent bond between the PVOH and the phenyl group of said indicator wherein said polymeric compositions are free of DMSO. The polymeric compositions are particularly suited for use in applications that benefit from the visible detection of microorganism contaminants and where avoidance of contamination and leaching by trace organic solvent or related materials associated with the indicator are desirable. Accordingly, a method for detecting whether food is spoiled or contaminated with microbes, using the polymeric compositions, is also provided.

DETAILED DESCRIPTION OF THE INVENTION

Throughout this application, the text refers to various embodiments relating to compounds, compositions, and methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the present invention.

Broadly, the present invention provides polymeric compositions comprising hydroxy phenyl pH indicators stably attached thereto through a covalent bond between the polyvinyl alcohol PVOH and the phenyl group of said indicator wherein said polymeric compositions are free of DMSO. The polymeric compositions described herein are particularly suited for use in applications that would benefit from the visible detection of microorganism contaminants and where avoidance of contamination and leaching by trace organic solvent or related materials associated with the indicator are desirable.

Avoiding trace organic solvent moieties is particularly useful where the polymeric compositions are in contact with edible foods, as the risk of potential deposition of trace organic solvents or organic solvent-derived materials onto the edible surfaces is avoided entirely. As further described below, the polymeric compositions of this invention are prepared using water as a solvent, rather than DMSO. Combined with the stable attachment of the present pH indicators, particularly via covalent bonding, the present polymeric compositions are well adapted for use in applications such as food packaging materials, as further illustrated herein. (The term "indicator film" is used from time to time herein and denotes particular film-like adaptations of the present polymeric compositions).

In one embodiment, there is provided a polymeric indicator comprising:
a) polyvinyl alcohol and
b) a plurality of hydroxy phenyl pH indicating moieties covalently bound to the polyvinyl alcohol backbone through a linking group that is attached at one end to a phenyl ring of the hydroxy phenyl pH indicating moiety and at another end to the polyvinyl alcohol backbone; wherein the pH indicating moieties undergo a detectable, colorimetric change in response to a pH change brought on by the presence of metabolic byproducts from microorganisms; and wherein the polymeric indicator is free from DMSO.

In some embodiments, the pH indicating moiety is an indicator formed from the reaction of a hydroxy phenyl pH indicator with a formylating agent. In some aspects the hydroxy phenyl pH indicator is phenol red. In other aspects the formylating agent is selected from the group consisting of formaldehyde, an aldehyde, and a homobifunctional aldehyde. In still other aspects the agent is formaldehyde or paraformaldehyde. In other aspects the homobifunctional aldehyde is glutaraldehyde.

In some embodiments, the linking group is an alkylene ether or an alkylene group. In some aspects the alkylene ether and alkylene groups contain from 1 to 20, 1 to 10, 1 to 5, or 1 to 3 methylene groups.

In some embodiments, the polymeric indicator is further free of other organic solvents.

In some embodiments, the polyvinyl alcohol has a molecular weight of 30,000 to 80,000 grams/mol and/or a thickness of 0.25 to 5 mil (one mil=1/1000 inch).

In some embodiments, the polymeric indicator is transparent. In still other embodiments the polymeric indicator is colored.

In some embodiments, pH change results from one or more types of microbes.

In some embodiments, the microbe is selected from the group consisting of but not limited to *Bacillus, Brucella, Campylobacter, Clostridium, Escherichia coli, Listeria monocytogenes, Salmonella, Streptococcus, Pseudomonas aeruginosa, Staphylococcus aureus, Shigella* spp., *Vibri* spp., *Yersini* spp. or a mixture of two or more such microbes.

In some embodiments, the polymeric indicator comprises covalently bound pH indicating moieties which undergo a detectable colorimetric change in response to a pH change resulting from the presence of an acid. In some aspects the acid is selected from the group consisting of but not limited to carbonic acid, sulfuric acid, and hydrogen sulfide.

In some embodiments, the acid is generated from a microbe or is formed by reaction of a gas generated from a microbe with water, said gas selected from the group consisting of carbon dioxide and sulfur dioxide.

In some embodiments provided is a method for detecting whether food is spoiled or contaminated with microbes such that said food is not edible, said method comprising:
a) placing a portion of said food proximal to the polymeric indicator;
b) detecting the presence or absence of a colorimetric change in the polymeric indicator; and
c) correlating the presence or absence of a colorimetric change in the polymeric indicator to whether the food is non-edible or edible.

In some embodiments provided is a food storage container containing the polymeric indicator. In some aspects the food storage container is a sealable bag. In other aspects the food storage container is a jug or bottle for storing liquids.

In some embodiments, the polymeric indicator is in the form of a flexible wrap comprising a first outer hydrophobic barrier layer an the polymeric indicating layer.

In some embodiments, the flexible wrap further comprises a third layer wherein said third layer is an inner barrier layer which is permeable to microbial byproducts but impermeable to molecules having a molecular weight of about 200 daltons or more, said second or middle layer is the polymeric indicator layer, and said first outer layer is a hydrophobic layer.

In some embodiments, the first layer is selected from the group consisting of polyethylene, polyethylene terephthalate, poly(vinylidene fluoride), poly(vinyl chloride), poly(vinylidene chloride), polypropylene, phenoxy resins, butadiene/styrene copolymers, butadiene/methylstyrene copolymers, poly(meth)acrylates, butadiene/acrylonitrile copolymers, ethylene/propylene copolymers, polybutadiene, polyisoprene, poly(oxy-2,6-dimethyl-1,4-phenylene), poly(oxycarbonyloxy-1,4-phenyleneisopropylidene-1,4-phenylene), acrylonitrile styrene copolymers, acrylonitrile/methyl acrylate/butadiene copolymers, acrylonitrile/styrene/butadiene copolymers, poly-1-vinylnaphthalene, polyvinylphenyl ketone, poly-p-xylenedodecanedioate, poly-tetramethylene octenediamide, poly-tetramethylene terephthalene, poly-trimethylene-3,3'-dibenzoate, poly-terephthallic anhydride, poly-4-methyl-diamine, polyvinylene carbonate, polyvinylene laurate, polyisopropenyl acetate, polyallylbenzene, polyvinylbutyl ether, polyvinyl formate, polyvinyl phenyl ether, polynorbornadine, polycarbonate, hydrophobic polyesters and polyurethanes, or a mixture thereof.

In some embodiments, the flexible wrap has incorporated into, attached thereto or printed thereon a machine recognizable code such as a barcode or a RFID (radio frequency identification) tag.

In another method aspect, there is provided a method for preparing the polymeric indicator according to the procedures disclosed herein.

Food or food stuff refer to any edible substance including solids and liquids such as meats, fish, vegetables, milk, milk products such as yogurt, cottage cheese, ice cream, etc., fruit and the like. Preferably, the food used in combination with the polymeric compositions of this invention are those which, when contaminated by microbes, provide for a detectable byproduct either from the food or the microbe that alters the pH of the food in a detectable manner.

In particular embodiments described further below, the pH indicator is employed in an amount effective for detecting a color change thereby evidencing a change in pH. As used herein, the term "detection" denotes a color-change either visible by human eye having ordinary vision or by instrumentation.

Hydroxy phenyl pH indicator refers to pH indicators having at least one phenyl group to which is attached a hydroxy group and includes di- and tri-phenylmethane indicators. One example is phenol red, which when reacted with formaldehyde and covalently bound to a PVOH, retains its reactivity characteristics to acid-base environmental changes through absorption of light at wavelengths between 490-510 nm being blue-green and 430-480 nm being blue exhibiting a visually perceptible color change to the indicator of red to yellow in which red indicates a neutral pH of 7 and yellow indicates an acid pH of 5 or lower. Other hydroxy phenyl pH indicators include bromocresol green.

As shown in the Examples, the pH indicating moieties may be prepared by reacting the hydroxy phenyl pH indicators with a formylating agent. The intermediates resulting from this reaction will have a linking group attached directly to the phenyl ring of the hydroxyl phenyl indicator. These intermediates may include monomers, dimers, trimers, tretramers, and other prepolymers or mixtures thereof where the respective number of hydroxy phenyl pH indicators are linked to each other serially with the linking group derived from the formylating agent. In some instances the linking group is a methylene ($CH_2$) group. Further reaction of the pH indicating moieties with PVOH allows a linking group at the terminal indicator (if the pH indicating moieties are not monomers) to be covalently bound to the PVOH backbone through the hydroxy group of the PVOH (thereby forming an ether) or through an alkylene group resulting from dehydration of the hydroxyl group of PVOH. The term "alkylene" refers to the divalent group —$(CH_2)_m$— where m can range from 1 to 20, 1 to 10, 1 to 5, or 1 to 3 methylene groups. The term "alkylene ether" refers a divalent alkylene group wherein at least one methylene group is replaced with oxygen.

The term "formylating agent" as used herein refers to a reagent containing at least one carbonyl group and includes formaldehyde, an aldehyde, and a homobifunctional aldehyde. Formaldehyde may be in the form of paraformaldehyde. The term "homobifunctional aldehyde" refers to reagents having at least two aldehyde groups. An example of a "homobifunctional aldehyde" is glutaraldehyde.

When the PVOH has a degree of deacetification of about 88±1%, and a molecular weight of between 30,000 to 80,000 grams/mol, then the amount of pH indicating moiety used for covalent binding to the PVOH is preferably between 1% to 5% by weight, and more preferably about 2.5±0.5%. PVOHs with different degrees of deacetylation and different molecular weights can be used for different purposes and the amount of indicator conjugate used under such circumstances should thus be optimized for those conditions. Indeed, polymers other than PVOH can be used for covalent binding with pH indicators and similar considerations should be given for optimization under such circumstances.

As the present invention contemplates the use of water for preparing the polymeric indicator, the risk of trace organic solvent moieties or secondary byproducts is eliminated. The term "solvent" is used in a chemistry context to mean the component of a solution that is present in the greatest amount. A "solvent" is the substance in which the solute is dissolved.

Thus, as conjugation of the pH indicating moeity and the polymer uses water as the solvent, the conjugated (covalently bound) product is essentially free of all organic solvent derived moieties. As used here, "essentially free" means that organic solvent derived moieties are undetectable using acceptable assay methods. Depending on the monomer/polymer composition, there may be trace materials which may incidentally overlap with organic solvent moieties, although the source of the trace materials is not an organic solvent. This is because many suitable polymeric moieties have carbon atoms, and such carbon atoms may themselves become degradation products of the polymeric composition. The present invention contemplates that such unavoidable carbon-based trace materials are not the organic solvent derived moieties (the polymeric composition is "essentially free" of such unavoidable carbon based artifacts from the polymeric backbone). An organic solvent specifically used in the preparation of the polymeric composition will be in much greater proportions, engendering the need for extreme measures (such as severe heat, drying, etc.) to remove them (and even then, there is no certainty that such materials will be removed sufficiently for food contact purposes, for example). Further the term solvent is not intended to include defoaming agents, acrylics, surfactants, and cross-linking agents. Certain of these components are shown in Example 3.

The polymeric pH indicators detect pH change associated with byproducts of microbial growth. These byproducts include, amongst others, gaseous carbon dioxide, hydrogen sulfide, sulfur dioxide, hydrogen, ammonium, lactate, and mixtures thereof. Mixtures of the byproduct with moisture result in the formation of acids such as carbonic acid, sulfuric acid, ammonium hydroxide, lactic acid, or mixtures thereof that react with the indicator to produce a color change. The term "byproducts" with reference to microbes, refer to the gases that are expelled from these microorganisms due to their natural growth of populations in numbers. Such gases can be in the vapor state or can combine with water or be hydrolyzed to form an acid such as sulfuric acid, carbonic acid, hydrogen sulfide or other gaseous or water vapor state which lowers the pH of the immediate environment with increasing concentrations of the gas vapor or water vapor combination.

Microbes detectable by the packaging materials include, amongst others, bacterial, viral and fungal microbes but the microbes are most preferably bacterial. Among bacterial microbes whose growth in food can be detected by the methods described herein include but are not limited to *Bacillus, Brucella, Campylobacter, Clostridium, Escherichia coli, Listeria monocytogenes, Salmonella, Streptococcus, Pseudomonas, Staphylococcus, Shigella* spp., *Vibrio* spp., *Yersinia* spp., coliform or spore forming bacteria and other food borne pathogens known to be involved in food contamination. Particular strains have been identified as associated with fresh vegetables. For example, *Escheria coli* O157:H7 was associated with prepackaged spinach: "Investigation of an *Escheria coli* O157:H7 Outbreak Associated with Dole Pre-Packaged Spinach," California Food Emergency Response Team Final Report, Mar. 21, 2007 (available from the California Department of Health Services, Food and Drug Branch, P.O. Box 997435, MS 7602, Sacramento, Calif. 95899-7435 and also available from U.S. Food and Drug Administration San Francisco District, 1431 Harbor Bay Parkway, Alameda, Calif. 94502.)

The present polymeric compositions may be configured so that there is an outer layer that serves the function of keeping unwanted moieties out of the range of detection of the pH indicator (optionally as well as other functions, as described herein). The outer layer is optional, and may depend on the use to which the present polymeric compositions may be put. The outer layer may be configured to prevent or limit the penetration of water or water vapor, or microorganisms, from the environment and into the package (or other area which may be detected by the pH indicator, for example). In some aspects the hydrophobic polymeric outer layer is a polymer selected from the group consisting of polyethylene, polyethylene terephthalate, poly(vinylidene fluoride), poly(vinyl chloride), poly(vinylidene chloride), poly(vinyl alcohol), polypropylene, polyethylene, phenoxy resins, butadiene/styrene copolymers, butadiene/methylstyrene copolymers, poly(meth)acrylates, butadiene/acrylonitrile copolymers, ethylene/propylene copolymers, polybutadiene, polyisoprene, poly(oxy-2,6-dimethyl-1,4-phenylene), poly(oxycarbonyloxy-1,4-phenyleneisopropylidene-1,4-phenylene), acrylonitrile styrene copolymers, acrylonitrile/methyl acrylate/butadiene copolymers, acrylonitrile/styrene/butadiene copolymers, poly-1-vinylnaphthalene, polyvinylphenyl ketone, poly-p-xylenedodecanedioate, poly-tetramethylene octenediamide, poly-tetramethylene terephthalene, poly-trimethylene-3,3'-dibenzoate, poly-terephthallic anhydride, poly-4-methyl-diamine, polyvinylene carbonate, polyvinylene laurate, polyisopropenyl acetate, polyallylbenzene, polyvinylbutyl ether, polyvinyl formate, polyvinyl phenyl ether, polynorbornadine, polycarbonate, hydrophobic polyesters and polyurethanes, and many other resins, or a mixture thereof. The outer layer is optically transparent so that the colorimetric change arising from microbial growth can be detected.

The polymeric solution in liquid form can then be cast into a film using any number of different coating technologies, including: air knife coating, curtain coating, gap coating (knife over roll, knife over blanket, floating knife, etc.), gravure coating (engraved roll, offset engraved roll), immersion (dip) coating, mayer bar (meyer bar, metering rod, wire wound rod), reverse roll coating (L-head, nip-fed, pan-fed), rotary screen, or slot die (slot, extrusion). The choice of which coating technology might be selected to create the film is determined, in part, by the desired characteristics of the resulting film (i.e., film thickness). Other factors such as viscosity, surface tension, dry speed, production costs, etc., can also have a bearing on selection of which coating technology might be selected to create the film.

For the commercial practicability, a meyer bar coating technology may be employed where a 2 to 5 mil wet film thickness, and preferably, a 4.0 mil wet film thickness of the PVOH solution is applied to a polyethylene film.

The metabolic byproducts that result from the increasing populations of one or more contaminating microbes in a packaged product will increase in concentration at the surface of the product in contact with or in close proximity to the pH indicator covalently bonded to the polymeric sheet of the packaging material such as polyvinyl alcohol (PVOH) or other appropriate polymeric material or composition resulting in a reaction with the pH indicator and exhibiting visually perceptible color change of the packaging material in the local area of the increasingly higher concentration of the microbial metabolic byproducts as the entire package material may or may not react and demonstrate a color change.

In certain embodiments, the packaging material for storing one or more products in a package comprises a package material made of a polymeric composition having one inner side or product surface contact side covalently bonded to an indicator and that said indicator being phenol red or other similar pH indicator with a dynamic range between pH 6 and pH 8 for color change and exhibits visually perceptible color change when exposed to the byproducts of microbial growth such as carbon dioxide, carbon monoxide, carbonic acid, hydrogen sulfide, sulfur dioxide, hydrogen or other gas containing an acidic compound within or at the surface of the food contained within the packaging material. Specifically, phenol red can be reacted with formaldehyde to produce hydroxylmethyl groups at selected sites, and then be covalently linked to a polymer such as polyvinyl alcohol (PVOH) via the hydroxylmethyl groups.

A variety of configurations of the polymeric compositions are provided. In one embodiment, the packaging material may be in the form of a roll of film that can be dispensed from a cardboard box with cutting edge top and allow for sheets of varying lengths to be dispensed and used for covering of certain products. In other embodiments the packaging material is dispensed from a large roll with heat sealability. In still other embodiments, the packaging material is in the form of a container or "baggie" with a resealable side or top and is used for storage of certain food products. Another configuration for the packaging material may be as a strip or polymer sheet or card that may be inserted into an illustration of one embodiment, where the polymeric composition comprises a pH indicator covalently bonded to a polymer such as polyvinyl alcohol (PVOH), the final product configuration may be manufactured using methods for film formation.

In still another embodiment, the polymer composition of this invention can be "sandwiched" between one or more inner and one or more outer layers, each used to provide certain functionalities. The inner layer(s) can be a transparent barrier layer that is permeable to the microbial byproducts but impermeable to larger molecules. See, e.g., U.S. Pat. No. 6,495,368, which is incorporated herein by reference in its entirety. The outer layer can be as described above, a transparent outer layer.

Food Spoilage Adaptation

For food spoilage, the present indicator is based on the concept of pH change caused by the presence of metabolic byproducts from microorganisms. The pH change can be caused by numerous sources, including: gases, liquids containing electrolytes, ions and molecules that influence pH like lactic acid, citric acid and ammonia. As the definition of pH is the negative log of the hydrogen ion concentration, used to express the acidity or alkalinity of a solution, moieties which effect this ionic concentration change may be detectable.

Food spoilage, as indicated by the presence of metabolic byproducts of microbes, causes a shift in color of the pH indicator and one of skill in the art will select the indicator with reference to the desired microbe or byproduct or pH range to be detected.

The embodiments of the invention relate to the detection of byproducts of contaminating microbes in a packaged food product. These food products may be within the group commonly known as the low acid foods comprising meats, poultry, dairy, seafood and the like. These low acid foods have an inherent pH of near neutral or pH 7 or between pH 7.4 and 6.2. Foods known to be within the class referred to as medium acid foods are soups and pasta and have an inherent pH of 4.5 to 5.0. Foods that are known to be within the class referred to as acid foods are fruits and vegetables with an inherent pH between 3.7 and 4.5. Food known to be within the class referred to as high acid foods include lemons and pickled products with an inherent pH of between 2.3 and 3.7. In certain embodiments, food products other than those within the low acid range that have a more acidic characteristic may not be included in the applicable food product packaging for use with certain embodiments of this invention when the inherent lower pH values of the foods cause a reaction with the pH indicator of the packaging material and signal a false-positive result. A variety of pH indicators functional over different pH ranges may be used either alone or in combination with one another.

In another embodiment, provided is use of the packaging material for monitoring and providing an early warning of possible microbial contamination of packaged food. The presence of metabolic byproducts from microorganisms is detected by a change in the color of the packaging material at the site of increasing concentrations of these byproducts.

Polymeric pH Indicator Composition Synthesis

A synthesis of phenol red covalently bound to polyvinyl alcohol (PVOH) is shown in Examples 1, 2, and 3.

Accordingly, in one embodiment provided is a process for preparing a polymeric composition comprising a plurality of phenol red pH indicators covalently bound to polyvinyl alcohol. Typically, phenol red is added to an aqueous formaldehyde ($H_2CO$) and sodium hydroxide (NaOH) solution and the resulting mixture is heated to a slow boil for approximately four hours to give a mixture of regioisomeric phenol red-formaldehyde (PRF) compounds where the hydroxylmethyl group is bound at various positions of the aromatic rings. Acid is then added to precipitate the PRF product that is then isolated by filtration. The PRF compounds are then mixed with PVOH in an aqueous solution, typically at 80-90° C. and stirred vigorously for approximately two hours to give the PRF pH indicators covalently bound to PVOH. The polymer is then spread on a metal plate and typically dried at 90° C. with the process repeated as necessary to achieve the desired thickness. The polymer is then cured, typically at 120° C., to form the water insoluble PVOH-PRF film.

In another embodiment, the curing step is not carried out and cross linking agents are instead added such as shown, for example, in Example 3.

The foregoing and other aspects of the embodiments disclosed herein may be better understood in connection with the following examples.

EXAMPLES

In the examples below as well as throughout the application, the following abbreviations have the following meanings If not defined, the terms have their generally accepted meanings g=Gram
IPA=Isopropyl Alcohol
L=Liter
M=Molar
° C.=Degrees Celsius
mg=Milligram
min=Minutes
mL=Milliliter
MW=Molecular Weight
m/z=Mass/Charge
PVOH=Polyvinyl Alcohol
RT=Room Temperature Example 1

Synthesis of Phenol Red-Formaldehyde (PRF)

To a 100 mL glass round-bottom flask equipped with a mechanical stirrer, magnetic stir bar, and condenser, containing purified water (6.0 mL) was added 37% formaldehyde solution (2.0 mL; 36.5-38.0% stabilized with 10-15% methanol, Alfa Aesar Catalog #33314) and 0.50 g sodium hydroxide pellets. The solution was mixed until the sodium hydroxide pellets dissolved. Phenol red, free acid (0.71 g; Dudley Corporation Catalog #9935, CAS#143-74-8) was then added. Parafilm was used to seal the connection between the flask and the condenser to minimize any solution evaporation. Using an electric mantle, the temperature was adjusted so that the contents of the flask were allowed to reflux at a slow boil for 4 hours with stirring. Another 2.0 mL of the formaldehyde solution was added and the reaction was allowed to continue for another 4 hours. The heat source was then removed and 5-10 mL of concentrated (36.5-38%) hydrochloric acid (Mallinckrodt Chemicals Catalog #MK558746) was added drop-wise very slowly to precipitate the phenol red-formaldehyde reaction product (PRF). The PRF product was filtered through Whatman 41 ashless filter paper via a funnel and dried at room temperature for 24 hours in a desiccator at 30-40° C.

The product was analyzed by dissolving a small amount (approximately 100 mg) in 20 mL of 95% ethanol, USP (AAper Alcohol and Company, 190 proof). To this solution was added a small volume (approximately 5 mL) of 50% citric acid solution (prepared using 99+% citric acid, Lancaster Catalog #4238, in purified water to obtain a pH of 5). A color shift from red to yellow was observed.

The PRF product was analyzed using Fourier Transformed Infrared Spectraphotometry (FTIR) with Attenuated Total Reflectance (ATR) and showed a characteristic peak appearing at approximately 3400 $cm^{-1}$. The comparator used is a conventional phenol red-formaldehyde compound from the software library. The product was also analyzed by mass spectrometry. The product (10 mg) was dissolved in IPA (10 mL). The solution was directly injected into a Waters ZMD Mass Spectrometer, scanning from 0-800 m/z and analyzing for the presence or absence of a peak at 355 corresponding to the phenol red starting material.

Example 2

Preparation of Polyvinyl Alcohol-Phenol Red-Formaldehyde (PVOH-PRF) Film

PVOH (4.0 g, Celvol 523, average MW=30,000, average degree of saponification=88.0%) was slowly added to 100 mL purified water and the solution was heated to 80-90° C. Water was used, rather than an organic solvent, to avoid any risk of trace organic solvent residue or organic solvent byproduct. Upon dissolution of the PVOH, phenol red-formaldehyde (PRF) conjugate of Example 1 (0.1 g) was added and rigorously stirred for two hours. The solution was then cooled to room temperature. A meyer bar coating apparatus was used to apply a 4.0 mil wet film thickness to a polyethylene film. The resulting indicator film was cured for 30 min. at 90° C. and then 2 hrs at 120° C. followed by cooling to room temperature.

Example 3

Preparation of Polyvinyl Alcohol-Phenol Red-Formaldehyde (PVOH-PRF) Film Without Curing To a 2 L beaker adapted with a mechanical stirrer and a heating mantle, purified water (600 g) was added followed by a defoaming agent (Surfynol DF-75, 0.011 g). The solution was stirred and the temperature raised to approximately 90° C. PVOH (Celvol 523, 90 g) was added and the mixture stirred until the PVOH is completely solubilized, at which time the PRF-conjugate (2.25 g) was added. The mixture was allowed to stir at 90° C. for approximately 2 hours. Heating was then discontinued and the remaining Surfynol DF-75 (0.011 g) added. The solution was then cooled to room temperature without mixing. Once at room temperature, the following were then added slowly with mixing in the following sequence: an acrylic (Airflex EF500, 270 g), a surfactant (Surfynol 420, 10 g), and a cross-linking agent (PZ-33 Polyaziridine, 27.7 g).

Example 4

Preparation of Polyvinyl Alcohol-Phenol Red (PVOH-Phenol Red) Film

Another indicator film was prepared according to the method described in Example 2 using phenol red rather than phenol red-formaldehyde (PRF) conjugate. The resulting indicator film leached all of the phenol red indicator when soaked for 24 hours in a 0.1 M solution of NaOH. This demonstrates that phenol red which is not stably bound (here, covalently bound) to the PVOH polymer will leach out of the indicator film.

Example 5

Food Storage Bag Adaptation

This is a prophetic example to illustrate a food storage bag for detecting the presence of bacterial metabolic byproducts.

Bag product manufacture and materials: The PVOH-PRF indicator film as prepared in Example 2 may be manufactured as a bag.

Bag product configuration for closure: The bag may be of a zip-lock type, or have another closure system allowing moisture to be trapped within the bag, so as to preserve the moisture of the food stuff.

Bag product size: Although any bag size may be used, this example is to illustrate a particular configuration for consumer use. For consumer-bagged spinach, a 48 ounce bag, optionally resealable, is fabricated. The bag may have optional clasps to reduce the inner volume if the consumer does not use the entire product at once. This will have the effect of concentrating any microbial byproducts which may be present or have arisen after the original opening of the bag. Local concentration of the microbial byproduct may have the ultimate effect of producing a stronger visual signal as the chromophores (in the phenol red indicator) may be more readily available for ionic saturation.

The embodiments and examples described above are not intended to limit the invention. It should be understood that numerous modifications and variations are possible in accordance with the principles of the present invention.

What is claimed is:

1. A method for detecting whether food is spoiled or contaminated with microbes such that said spoiled or contaminated food is not edible, said method comprising:
   a) placing a portion of said food proximal to a polymeric indicator comprising:
      i) polyvinyl alcohol and
      ii) a plurality of hydroxy phenyl pH indicating moieties covalently bound to the polyvinyl alcohol backbone through a linking group that is attached at one end to a phenyl ring of the hydroxy phenyl pH indicating moiety and at another end to the polyvinyl alcohol backbone;
      wherein the pH indicating moieties undergo a detectable, colorimetric change in response to a pH change brought on by the presence of metabolic byproducts from microorganisms;
      and wherein the polymeric indicator is free from DMSO;
   b) detecting the presence or absence of a colorimetric change in the polymeric indicator; and
   c) correlating the presence or absence of a colorimetric change in the polymeric indicator to whether the food is non-edible or edible;
   wherein the linking is selected from the group consisting of a C1-C20 akylene group, a C1-C19 alkylene ether group, or the reaction product of formaldehyde, paraformaldehyde or glutaraldehyde with the hydroxy phenyl pH indicating moieties and the polyvinyl alcohol.

2. The method of claim 1, wherein the linking group is a reaction product of formaldehyde, paraformaldehyde or glutaraldehyde with the hydroxy phenyl pH indicating moieties and the polyvinyl alcohol.

* * * * *

UNITED STATES PATENT AND TRADEMARK OFFICE
CERTIFICATE OF CORRECTION

PATENT NO. : 8,637,271 B2  Page 1 of 1
APPLICATION NO. : 12/741268
DATED : January 28, 2014
INVENTOR(S) : Booher et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 748 days.

Signed and Sealed this
Twenty-second Day of September, 2015

Michelle K. Lee
*Director of the United States Patent and Trademark Office*